US00PP20319P2

(12) United States Plant Patent
Jandrew

(10) Patent No.: US PP20,319 P2
(45) Date of Patent: Sep. 15, 2009

(54) ***PENSTEMON* PLANT NAMED 'PENI MAG09'**

(50) Latin Name: *Penstemon hartwegii benth*
Varietal Denomination: Peni Mag09

(75) Inventor: Jason Jandrew, Gilroy, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 12/229,565

(22) Filed: Aug. 25, 2008

(51) Int. Cl.
*A01H 5/00* (2006.01)

(52) U.S. Cl. ..... Plt./465

(58) Field of Classification Search ..... Plt./263, Plt./465
See application file for complete search history.

*Primary Examiner*—Annette H. Para
*Assistant Examiner*—Susan B McCormick Ewoldt
(74) *Attorney, Agent, or Firm*—S. Matthew Edwards

(57) ABSTRACT

A new *Penstemon* plant named 'Peni Mag 09 ,' particularly distinguished by the large, white flower color with a bold red-purple margin, upright and semi-compact plants, strong stems, and earlier flowering habit.

1 Drawing Sheet

Latin name of the genus and species of the plant claimed *Penstemon hartwegii benth.*

Varietal denomination 'Peni Mag09'.

BACKGROUND OF THE NEW PLANT

The present invention comprises a new *Penstemon*, botanically known as *Penstemon hartwegii*, and hereinafter referred to by the variety name 'Peni Mag09.'

'Peni Mag09' is a product of a planned breeding program. The new cultivar 'Peni Mag09' has large, white flower color with a bold red-purple margin, upright and semi-compact plants, strong stems, and earlier flowering habit.

'Peni Mag09' originated from a hybridization in a controlled breeding program in Gilroy, Calif. USA. The female parent was an unpatented hybrid seedling identified as '11-1' with dusty rose color. '11-1' has a taller plant habit and is later to flower than 'Peni Mag09.'

The male parent of 'Peni Mag09' was an unpatented hybrid seedling identified as '104-1' with apple blossom flower color. '104- 1' has a taller plant habit and is later to flower than 'Peni Mag09.'

'Peni Mag09' was selected as one flowering plant within the progeny of the stated cross in 2006 in a controlled environment in Gilroy, Calif. USA.

The first act of asexual reproduction of 'Peni Mag09' was accomplished when vegetative cuttings were taken from the initial selection in April of 2006 in a controlled environment in Gilroy, Calif. USA. The pollination was made in July 2005 and the seed sowing took place in October 2005 in a controlled environment in Gilroy, Calif. USA.

Horticultural examination of plants grown from cuttings of the plant initiated in April of 2006 in Gilroy, Calif. USA, and continuing thereafter, has demonstrated that the combination of characteristics as herein disclosed for 'Peni Mag09' are firmly fixed and are retained through successive generations of asexual reproduction.

'Peni Mag09' has not been observed under all possible environmental conditions. The phenotype may vary significantly with variations in environment such as temperature, light intensity and day length.

A Plant Breeder's Right for this cultivar was applied for in Canada on Dec. 24, 2007. 'Peni Mag09' has not been made publicly available more than one year prior to the filing of this application.

DESCRIPTION OF THE DRAWING

The accompanying photographic drawing shows typical flower and foliage characteristics of 'Peni Mag09' with colors being as true as possible with an illustration of this type. The photographic drawing shows a flowering potted plant of the new variety

DETAILED BOTANICAL DESCRIPTION

The measurements were taken in April, 2008, on plants that were growing in 1 gallon pots in a greenhouse in Gilroy, Calif. USA. Culture of these plants started in about January 2008 in a greenhouse. The plants were about 4 months old.

Color Chart used: Royal Horticultural Society Colour Chart (R.H.S.) 2001

BRIEF SUMMARY OF INVENTION

The following observations, measurements, and comparisons describe plants grown in a greenhouse in Gilroy, Calif. USA. The following traits have been repeatedly observed and are determined to be basic characteristics of the new variety. The combination of these characteristics distinguishes this *Penstemon* as a new and distinct variety.

TABLE 1

DIFFERENCES BETWEEN THE NEW VARIETY 'PENI MAG09' AND A SIMILAR VARIETY

| | 'Peni Mag09' | 'Pheni Mag' (U.S. Plant Pat. No. 17,987) |
|---|---|---|
| Flowering response | Earlier | Later |
| Plant habit | More compact | Less compact/taller |
| Flower color (margins) | Slightly less bold | Little bolder |

Plant:

*Form, growth and habit.*—Upright, semi-compact, strong branching and vigor.

*Plant height.*—27–31 cm.

*Plant height* (*inflorescence included*).—40–45 cm.

*Plant width.*—26–30 cm.

Foliage:

*Arrangement.*—Opposite and decussant.

*Immature, leaf color, upper surface.*—Closest to RHS 146B Lower surface: Closest to RHS 147B.

*Mature, leaf color, upper surface.*—RHS 146A but a little darker green Lower surface: Closest to RHS 147B.

*Length.*—12–13.5 cm.

*Width.*—3.4–3.7 cm.

*Shape.*—Lanceolate.

*Base.*—Accuminate.

*Apex shape*—Acute.

*Margin.*—Slightly and irregularly serrulate.

*Texture.*—Glabrous on both sides.

*Color of veins, upper surface.*—RHS 144C.

*Color of veins, lower surface.*—RHS 144C.

Stem:

*Number of main stems per plant.*—5–6.

*Number of leaves per branch.*—18–20 .

*Color of stem.*—RHS 144B, with some anthocyanin of a subdued hue of RHS 183B.

*Length of stem.*—30–34 cm.

*Diameter.*—0.4–0.5 cm.

*Length of internodes.*—0.4–0.7 cm.

*Texture.*—Some pubescence.

Inflorescence

*Type.*—On first flowering it appears to be a raceme, then matures to more of a thyrse with short peduncles emerging at the nodes in opposite arrangement, each peduncle bearing 3–4 flowers or buds at various stages of development; the flowers are held somewhat horizontally.

*Blooming habit.*—Intermittent; removing of spent flowers enhances development of new flowers.

*Number of inflorescences per plant.*—10–14; early terminal pinching of apices enhances formation of more racemes.

*Raceme color.*—RHS 144B.

*Raceme length.*—16–21 cm.

*Raceme texture.*—Some pubescence.

*Color of peduncle.*—RHS 144B with anthocyanins of RHS 176B on the upper surface only.

*Length of peduncle.*—0.7–0.8 cm.

*Diameter of peduncle.*—0.2 cm.

*Texture.*—Some pubescence.

*Color of pedicel.*—RHS 144B.

*Length of pedicel.*—0.5–0.6 cm.

*Diameter of pedicel.*—0.1 cm.

*Texture.*—Pubescent to hirsute.

Corolla:

*Form.*—Zygomorphic and single; funnel shaped with the petals fused at base, 5 free lobed, opening outward.

*Fragrance.*—None.

*Lastingness of individual florets.*—About 7 days.

*Width of floret.*—5.1–5.4 cm.

*Depth of floret.*—4.5–4.6 cm.

*Color upper lobes, upper surface.*—N155B but a little whiter, a wide band of RHS 60B around the margins.

*Color upper lobes, lower surface.*—RHS N155B but a little whiter, a wide band of RHS 60C around the margins.

*Length of upper lobes.*—1.1–1.2 cm.

*Width of upper lobes.*—1.7–1.8 cm.

*Color lateral lobes, upper surface.*—Same as upper.

*Color lateral lobes, lower surface.*—Same as upper.

*Length of lateral lobes.*—1.4–1.5 cm.

*Width of lateral lobes.*—1.6–1.8 cm.

*Color lower mid-lobe, upper surface.*—Same as upper.

*Color lower mid-lobe, lower surface.*—Same as upper.

*Length of lower mid-lobe.*—1.2–1.3 cm.

*Width of lower mid-lobe.*—1.6–1.8 cm.

*Apex shape.*—Rounded.

*Margin.*—Entire.

*Petal texture.*—Pubescent; glandular hairs on both surfaces.

*Corolla color, inside.*—RHS N155B but whiter.

*Corolla color, outside.*—RHS 60C on the top, RHS 60D on the bottom; with RHS N 155B basally at the calyx.

*Corolla length.*—3.5–3.7 cm.

Bud (just before opening):

*Color.*—RHS 60A.

*Length.*—1.5–2.3 cm.

*Width.*—0.7–0.8 cm.

*Shape.*—Oblong.

Calyx:

*Number of sepals.*—5, fused at base.

*Color of sepals.*—RHS 144B; sometimes with a hint of anthocyanins of RHS N79C at the margins.

*Length of sepals.*—1.1–1.2 cm.

*Width of sepals.*—0.3–0.6 cm.

*Sepal shape.*—Ovate.

*Apex shape.*—Acute.

*Margins.*—Entire.

*Texture.*—Pubescent; some glandular hairs on both surfaces.

Reproductive organs:

*Pistil.*—1 .

*Style color.*—RHS N155B but whiter at the apex; RHS N74C basally.

*Style length.*—3.0–3.1 cm.

*Stigma color.*—RHS 144C.

*Number of anthers.*—5; 4 of which are fertile.

*Color of filaments.*—RHS N155C.

*Length filaments.*—2.8–3.4 cm.

*Pollen amount.*—Abundant.

*Color of pollen.*—RHS N155B.

*Fertility/seed set.*—Not observed on this hybrid.

Disease/pest resistance: Disease resistance or susceptibility has not been observed on this hybrid.

What is claimed is:

1. A new and distinct variety of *Penstemon* plant named 'Peni Mag09,' substantially as illustrated and described herein.

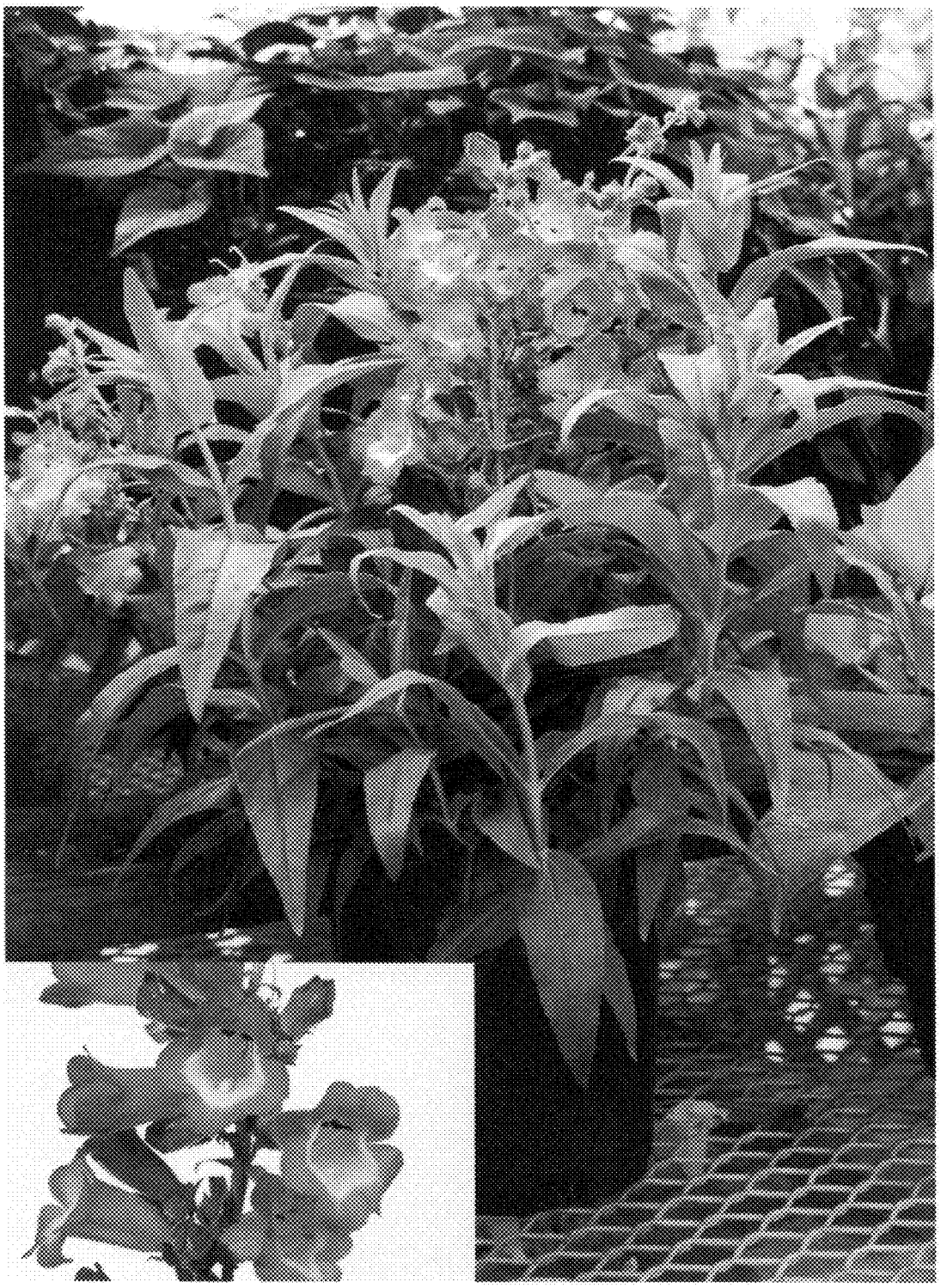

* * * * *